United States Patent [19]

Gray et al.

[11] 4,340,765

[45] Jul. 20, 1982

[54] 4-PHENOXY-2-BUTENE DERIVATIVES AS PLANT GROWTH REGULATORS

[76] Inventors: Gary M. Gray, Bethlehem, Pa.; George Schwartzkopf, Jr., Franklin Township, N.J.; J. T. Baker Chemical Co., 02, Phillipsburg, N.J.

[21] Appl. No.: 178,080

[22] Filed: Aug. 14, 1980

[51] Int. Cl.³ .............................................. C07C 59/48
[52] U.S. Cl. .......................................... 71/123; 560/9; 560/20; 560/56; 560/142; 560/144; 562/426; 562/433; 562/434; 562/438; 562/451; 562/466; 562/471; 562/472; 564/161; 564/162; 564/163; 564/166; 564/169; 568/441; 568/478; 71/108; 71/98; 568/41; 568/442
[58] Field of Search .......................... 560/62; 562/472; 71/108; 568/442, 424, 41

[56] References Cited

U.S. PATENT DOCUMENTS

| | | | |
|---|---|---|---|
| 1,716,822 | 6/1929 | Knorr et al. | 568/442 |
| 2,500,582 | 3/1949 | Smith et al. | 568/442 |
| 3,362,997 | 1/1968 | Bolhofer | 568/442 |
| 3,363,003 | 1/1968 | Bolhofer | 568/442 |
| 3,452,081 | 6/1969 | Sprague | 560/62 |
| 3,453,317 | 7/1969 | Marbet et al. | 568/442 |
| 4,163,661 | 8/1979 | Jikihara | 560/62 |

FOREIGN PATENT DOCUMENTS 1162767  8/1969  United Kingdom .................. 560/62

OTHER PUBLICATIONS

Derwent Abstract 67524Y–Japan Kokai, 77 94 241, filed Jan. 27, 1976, published Aug. 9, 1977.
Derwent Abstract 33642C–Japan Kokai, 80 43, 048, filed Sep. 22, 1978, published Mar. 26, 1980.
Derwent Abstract 73563A–Japan Kokai, 78 101 320, filed Feb. 17, 1977, published Sep. 4, 1978.
Derwent Abstract 73622A–Japan Kokai, 101, 525, filed Feb. 17, 1977, published Sep. 5, 1978.

*Primary Examiner*—Paul J. Killos
*Attorney, Agent, or Firm*—George W. Rauchfuss, Jr.

[57] ABSTRACT

4-Phenoxy-2-butene derivatives are disclosed as inhibitors of cytokinin plant growth regulatory activity and as possessing seed germination regulatory properties and senescence delaying activity when applied to plants. 4-Phenoxy-2-butene derivatives can also be useful as plant dwarfing agents, agents to retard seedling development or as herbicides.

26 Claims, No Drawings

4-PHENOXY-2-BUTENE DERIVATIVES AS PLANT GROWTH REGULATORS

FIELD OF THE INVENTION

This invention relates to 4-phenoxy-2-butene derivatives, their use as plant growth regulating agents and to plant growth regulating compositions of said compounds.

SUMMARY OF THE INVENTION

According to the present invention it has been discovered that 4-phenoxy-2-butene derivatives of the general formula

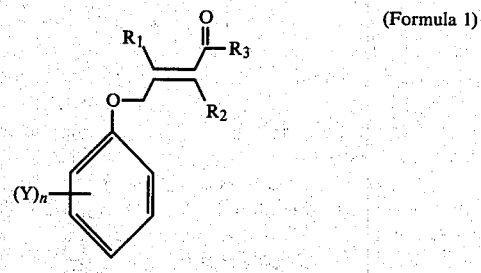

(Formula 1)

and phytopharmaceutically acceptable salts thereof, wherein $R_1$ and $R_2$ are selected from hydrogen and —$CH_3$ with the proviso that one of $R_1$ and $R_2$ is —$CH_3$ and the other is hydrogen; $R_3$ is selected from the group consisting of hydrogen, hydroxy, (lower)alkyl, amino, —O—(lower)alkyl, —S—(lower)alkyl, —NH—(lower)alkyl, or —N—di(lower)alkyl; Y is selected from the group consisting of (lower)alkyl, halo, nitro, —$CF_3$, —S—(lower)alkyl, —O—(lower)alkyl, —O—acetyl, hydroxy, —NH—acetyl, amino, —NH(lower)alkyl, —N—di(lower)alkyl, and a fused benzene ring; and n is equal to 0, 1 or 2; have plant growth regulating activity. The term (lower)alkyl as used in the foregoing definitions is meant to include straight or branched chain alkyl radicals containing from 1 to 6 carbon atoms, such as, for example, methyl, butyl, hexyl, 1-methylethyl and the like. Although the halo atom can be any suitable halogen atom, Y is preferably chlorine or bromine.

The phytopharmaceutically acceptable salts can be salts of the appropriate derivatives with inorganic or organic acids, such as, for example, hydrochloric, nitric, sulfuric, chloric, thiocyanic, phosphoric, acetic, p-toluenesulfonic, oxalic, methanesulfonic, ethanesulfonic, naphthalenesulfonic acid and the like.

The 4-phenoxy-2-butene derivatives and phytopharmaceutically acceptable salts thereof inhibit cytokinin plant growth regulating activity and also seed germination regulatory properties or senescence delaying activity when applied to plants in plant growth regulating amounts. The 4-phenoxy-2-butene derivatives and phytopharmaceutically acceptable salts thereof have also been found to possess plant dwarfing activity when applied to plants in plant dwarfing effective amounts and herbicidal activity when applied in herbicidally effective amounts.

DETAILED DESCRIPTION OF THE INVENTION

The 4-phenoxy-2-butene derivatives of this invention have been found to possess plant growth regulating activity when employed in effective plant growth regulating amounts. The compounds of the present invention are generally active plant growth regulants when applications of from about 0.05 kg/hectare to about 20 kg/hectare of the compound is employed and preferably from about 0.1 kg to about 5 kg/hectare.

Especially preferred as plant growth regulating compounds of this invention are compounds of the general formula

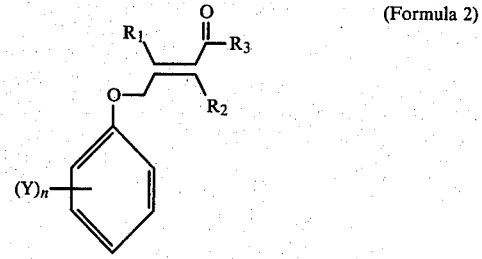

(Formula 2)

and phytopharmaceutically acceptable salts thereof wherein $R_1$ and $R_2$ are selected from hydrogen and —$CH_3$ with the proviso that one of $R_1$ and $R_2$ is —$CH_3$ and the other is hydrogen; $R_3$ is selected from hydrogen, hydroxy and —O—(lower)alkyl; Y is selected from the group consisting of halo, —O—(lower)—alkyl, —O—acetyl, hydroxy, —NH—acetyl and a fused benzene ring; and n is equal to 1 or 2, preferably 1. It is also preferred that when Y is halo, Y is chlorine and then preferably n is equal to 2 and the Y's are in the 2- and 4-positions on the phenyl ring.

As examples of plant growth regulating compounds of this invention there may be mentioned, for example (E)-4(4-acetamidophenoxy)-2-methyl-2-buten-1-al
(E)-4(3-acetamidophenoxy)-2-methyl-2-buten-1-al
(E)-4(3-methoxyphenoxy)-2-methyl-2-buten-1-al
(E)-4(4-methoxyphenoxy)-2-methyl-2-buten-1-al
(E)-4(2,4-dichlorophenoxy)-2-methyl-2-buten-1-al
methyl (E)-4(2,4-dichlorophenoxy)-2-methyl-2-buten-1-oate
(E)-4(2,4-dichlorophenoxy)-2-methyl-2-buten-1-oic acid
(E)-4(3-acetoxyphenoxy)-2-methyl-2-buten-1-al
(E)-4(3-hydroxyphenoxy)-2-methyl-2-buten-1-al
(E)-4(4-hydroxyphenoxy)-2-methyl-2-buten-1-al
(E)-4(1-naphthyloxy)-2-methyl-2-buten-1-al
(E)-4(4-trifluoromethylphenoxy)-2-methyl-2-buten-1-al
(E)-4(4-methylphenoxy)-2-methyl-2-buten-1-al
(E)-4(4-methylthiophenoxy)-2-methyl-2-buten-1-al
(E)-4(2,4-dichlorophenoxy)-3-methyl-2-buten-1-al
(E)-4(4-aminophenoxy)-2-methyl-2-buten-1-al
(E)-4(4-ethylaminophenoxy)-2-methyl-2-buten-1-al
(E)-4(4-dimethylaminophenoxy)-2-methyl-2-buten-1-al
(E)-4(4-nitrophenoxy)-2-methyl-2-buten-1-al
(E)-4(3-butoxyphenoxy)-2-methyl-2-buten-1-al
(E)-5-phenoxy-3-methyl-2-oxo-3-pentene butyl (E)-4(2,4-dichlorophenoxy)-2-methyl-2-buten-1-oate
(E)-4(2,4-dichlorophenoxy)-2-methyl-2-buten-1-amide
(E)-4(2,4-dichlorophenoxy)-2-methyl-2-buten-1-dimethylamide methyl (E)-4(3-hydroxyphenoxy)-2-methyl-2-buten-1-oate
(E)-4(2,4-dichlorophenoxy)-2-methyl-2-buten-1-ethylamide
(E)-4-phenoxy-2-methyl-2-buten-1-al methyl (E)-4(methoxyphenoxy)-2-methyl-2-buten-1-thioate The compounds of this invention wherein $R_3$ is hydrogen are generally prepared, for example, by the reaction of equimolar amounts of an appropriate phenol of the formula

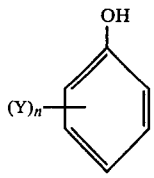

(Formula 3)

and (E)-4-halo-1,1-diethoxy-2-methyl-2-butene derivative of the formula

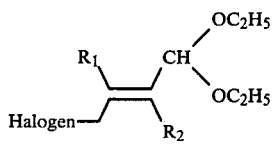

(Formula 4)

in the presence of excess potassium carbonate at ambient temperature or by heating for from about 1 to 48 hours under a nitrogen atmosphere and in dry N,N-dimethylformamide wherein Y, n, $R_1$ and $R_2$ are as first defined hereinbefore and Halogen is chlorine or bromine, preferably bromine. The reaction mixture is poured into water (10:1) and the acetal is extracted with diethylether and the ether solution is evaporated to dryness and the acetal reaction product is hydrolyzed in an acetone/water mixture with p-toluenesulfonic acid as a catalyst to yield the desired product.

The compounds of this invention wherein $R_3$ is —O—(lower)—alkyl may be prepared, for example, by oxidation of the corresponding aldehyde compound wherein $R_3$ is hydrogen. Oxidation of the aldehyde is accomplished, for example, by the use of a manganese dioxide/sodium cyanide oxidation reaction system in the presence of acetic acid and methanol.

The compounds of this invention wherein $R_3$ is hydroxy may be prepared, for example, by the base catalyzed hydrolysis of the corresponding compound wherein $R_3$ is —O—(lower)—alkyl. Hydrolysis of the compound wherein $R_3$ is —O—(lower)—alkyl is accomplished, for example, by the use of a 20% solution of potassium hydroxide in methanol.

The compounds of the invention wherein $R_3$ is amino, —NH—(lower)alkyl, —N—di(lower)alkyl or —S—(lower)alkyl may be prepared, for example, by the reaction of the corresponding compound wherein $R_4$ is Cl with the appropriate amino or thiol compound in methylene chloride in the presence of 4-dimethylaminopyridine. When the corresponding compound wherein $R_4$ is OH is employed as the reactant, the reaction is also run in the presence of N,N-dicyclohexylcarbodiimide. The reaction scheme is as follows:

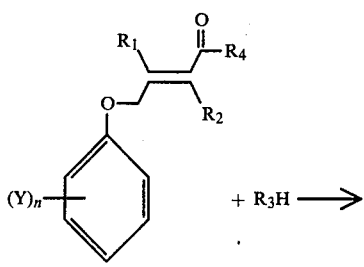

+ $R_3H$ →

-continued

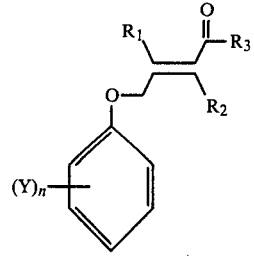

wherein $R_4$ is OH or Cl and $R_3$ is amino, —NH—(lower)alkyl, —N—di(lower)alkyl or —S—(lower)alkyl and $R_1$, $R_2$, Y and n are as first defined hereinbefore.

It will also be apparent to those skilled in the art that various desired compounds of this invention can be produced from other compounds of this invention by conventional conversion techniques, such as, for example, compounds wherein Y is hydroxy may be prepared from the corresponding compounds wherein Y is O-acetyl by the base catalyzed hydrolysis of a corresponding O-acetyl substituted compound by employing, for example, a 5% aqueous sodium hydroxide solution.

As examples of preparations of compounds of this invention, reference may be had to the following Examples.

EXAMPLE 1

(E)-4(4-Acetamidophenoxy)-2-methyl-2-buten-1-al

A solution of 1.0 g (E)-4-bromo-1,1-diethoxy-2-methyl-2-butene in 10 ml of sieve dried dimethyl formamide is treated with 0.7 g of p-acetylaminophenol and 0.64 g anhydrous potassium carbonate. The suspension is stirred under nitrogen for four days and the mixture is then poured into 100 ml water and the hazy solution extracted with two 100 ml portions of benzene. The benzene extract is washed with water and dried with sodium sulfate. The benzene extract is concentrated and vacuum dried to give 0.75 g of (E)-4-(4-acetylaminophenoxy)-1,1-diethoxy-2-methyl-2-butene which is dissolved in about 5 to 10 ml acetone and treated with about 1 ml water and a spatula of p-toluenesulfonic acid monohydrate. The resulting solution is agitated occasionally for 30 minutes and the solution is evaporated at room temperature giving a solid, ethylether insoluble residue. The residue is dissolved in about 150 ml methylene chloride and washed twice with water. The residue is dried with sodium sulfate and concentration gave 0.45 g of a solid. The material is filtered in about 50 ml of hot carbon tetrachloride-benzene then boiled down to about 10 ml. The product is filtered and washed with room temperature carbon tetrachloride giving 0.2 g white solid, m.p. 127°-30° C. Elemental Analysis. Calculated for $C_{13}H_{15}NO_3$: C,66.94; H,6.48; N,6.00. Found: C,66.64; H,6.29; N,5.75.

EXAMPLE 2

(E)-4(3-Acetamidophenoxy)-2-methyl-2-buten-1-al

A mixture of 12.6 g of crude (E)-4-bromo-1,1-diethoxy-2-methyl-2-butene diluted to 100 ml with sieve dried dimethyl formamide, 8.8 g of 3-acetylaminophenol and 8.1 g of anhydrous potassium carbonate is stirred at room temperature under nitrogen for about 75 hours and is then diluted to 500 ml with water and extracted with three 100 ml portions of benzene. Concentration of the benzene extract gives 7.2 g of brown oil which is dissolved in 72 ml acetone and 14 ml water and treated with 1.4 g of p-toluenesulfonic acid monohydrate and agitated occasionally for about 30 minutes. Acetone is then stripped at room temperature. The residue is treated with 75 ml benzene and 75 ml methylene chloride. This mixture is extracted with 70 ml of 10% aqueous potassium carbonate. The lower organic layer is drawn off and the aqueous layer plus emulsion is extracted with two 75 ml portions of methylene chloride. The organic phases are combined, washed once with about 75 ml water and dried with sodium sulfate. Concentration gives 4.1 g solid residue. The residue is recrystallized from benzene, final volume about 25 ml, giving 1.4 g of solid (E)-4(3-acetaminophenoxy)-2-methyl-2-buten-1-al, m.p. 119°–25° C.

EXAMPLE 3

(E)-4(2,4-Dichlorophenoxy)-2-methyl-2-buten-1-al

In 100 ml dimethylformamide there is combined 34.9 g (E)-4-bromo-1,1-diethoxy-2-methyl-2-butene, 24.0 g 2,4-dichlorophenol, 40.5 g potassium carbonate and 2.37 g potassium iodide and stirred under nitrogen for about five hours. The resulting solution is poured into 500 ml deionized water and the solution extracted with two 200 ml portions diethylether which are then combined and washed first with 300 ml 10% aqueous potassium carbonate solution and then with three 400 ml portions of deionized water. The ether solution is treated with magnesium sulfate and activated charcoal then filtered. The filtrate is evaporated to dryness and the yellow-brown oil is taken up in a mixture of 120 ml acetone and 20 ml water and stirred under nitrogen as 3.0 g p-toluenesulfonic acid is added. Thirty minutes after the addition, the solution is evaporated to dryness and the residue taken up in 200 ml diethylether and this solution washed with two 200 ml portions deionized water. The ether solution is treated with magnesium sulfate and activated carbon and then filtered. The filtrate is evaporated to dryness to yield 31.47 g purple oil which is purified by chromatography on a Waters Prep. 500 LC using a silica gel cartridge yielding 25.31 g of a yellow oil. The oil is recrystallized from diethylether-hexane yielding 18.22 g solid product, m.p. 58.5°–59.5° C. Elemental Analysis. Calculated: C,53.90; H,4.11; Cl,20.93. Found: C,53.86; H,4.00; Cl,28.78.

EXAMPLE 4

(E)-4(3-Methoxyphenoxy)-2-methyl-2-buten-1-al

A mixture of 12.65 g of crude (E)-4-bromo-1,1-diethoxy-2-methyl-2-butene, 6.4 ml of m-methoxyphenol, and 8.1 anhydrous potassium carbonate in 100 ml sieve dried dimethylformamide is stirred at room temperature under nitrogen for about 43 hours and the reaction mixture diluted to 500 ml with water and extracted with a 300 ml and two 100 ml portions of hexane. The combined hexane extracts are washed with two portions of brine and dried with sodium sulfate. Concentration of the hexane extracts yields 6.45 g (E)-1,1-diethoxy-(4-m-methoxyphenoxy)-2-methyl-2-butene.

A solution of 12.3 g (E)-1,1-diethoxy-4-m-methoxyphenoxy)-2-methyl-2-butene is dissolved in 125 ml acetone and treated with 25 ml water and 2.5 g p-toluenesulfonic acid monohydrate and stirred under nitrogen for 2 hours. The solution is concentrated at room temperature and the two-phase residue extracted with 100 ml benzene. The benzene extract is washed with 25 ml of 10% aqueous potassium carbonate followed by 25 ml water, dried with sodium sulfate and concentrated to yield 0.5 g orange oil which is chromatographed on a Waters LC/500 HPLC using a 500 gm silica column using 10% diethylether-hexane. Recrystallization of the product fraction from hexane containing a small portion of diethylether yields 0.23 g of the desired product. m.p. 45°–8° C. Elemental Analysis. Calculated for $C_{12}H_{14}O_3$: C,69.88; H,6.84. Found: C,69.51; H,6.59.

EXAMPLE 5

Methyl (E)-4(2,4-Dichlorophenoxy)-2-methyl-2-buten-1-oate

In 80 ml of methanol 2.45 g (E)-4(2,4-dichlorophenoxy)-2-methyl-2-buten-1-al, 14.6 g of active manganese dioxide, 2.52 g sodium cyanide and 0.92 g acetic acid are combined under nitrogen and the mixture stirred at room temperature for about 16 hours. The reaction mixture is vacuum filtered to remove the manganese dioxide and then evaporated to dryness using an aspirator trapped with sodium hydroxide solution and a hot water bath which did not exceed 50° C. Upon removal of all the solvent the residue is taken up in a mixture of 100 ml water and 100 ml methylene chloride and the phases separated. The organic phase is washed with three 100 ml portions of water, dried over magnesium sulfate and filtered. The filtrate is evaporated to dryness to yield 2.71 g of oily yellow solid residue. The residue is dissolved in 50 ml hot ether and the solution heated under a stream of nitrogen as 10 ml hexane is added. When the volume of the solution reaches 40 ml, it is filtered through a 1 cm column of silica gel in a 30 cc fritted glass filter. The filtrate is placed in a freezer and a white crystalline solid forms which is collected by nitrogen pressure filtration and washed with 10 ml of a 1:1 mixture of ether and hexane. After drying on the filter 0.38 g of white fluffy solid product is obtained, m.p. 92°–93° C. Elemental Analysis. Calculated: C,52.39; H,4.40; Cl,25.77. Found: C,52.20; H,4.32; Cl,26.01.

EXAMPLE 6

(E)-4(2,4-Dichlorophenoxy)-2-methyl-2-buten-1-oic acid

In 20 ml of a 1:1 tetrahydrofuran-methanol mixture 0.38 g methyl (E)-4(2,4-dichlorophenoxy)-2-methyl-2-buten-1-oate is dissolved and the solution stirred under nitrogen as a 20% aqueous potassium hydroxide solution is added dropwise. The solution is then heated at reflux for about 2 hours before being evaporated to dryness. The residue is taken up in 20 ml water and filtered to remove the very small amount of insoluble material and is then acidified with dropwise addition of dilute aqueous HCl. The mixture is extracted with two 20 ml portions of methylene chloride and the extracts are combined and treated with magnesium sulfate and the mixture filtered. The filtrate is heated under a stream of nitrogen as 5 ml of hexane is added. When the volume reaches 10 ml the solution is allowed to cool to room temperature and is placed in a freezer. A white needle-like crystalline solid forms and is collected by nitrogen pressure filtration and after drying on the filter 0.11 g solid product is collected, m.p. 117°–121.5° C.

EXAMPLE 7

(E)-4(3-Acetoxyphenoxy)-2-methyl-2-buten-1-al

A mixture of 8.17 g (E)-4-bromo-1,1-diethoxy-2-methyl-2-butene, 5.24 g resorcinol monoacetate and 9.50 g potassium carbonate in 50 ml sieve-dried dimethyl formamide is stirred at room temperature for about 3 hours and the solution poured into a mixture of 200 ml saturated potassium carbonate solution and 300 ml ice and stirred until the ice has melted. The solution is then extracted with two 200 ml portions of diethylether and the extracts combined, washed with four 500 ml portions of deionized water and the extracts combined, washed with four 500 ml portions of distilled water, dried with mangesium sulfate and treated with activated charcoal. The solution is filtered and the filtrate evaporated to dryness to yield 8.53 g of a yellow-brown oil. The oil is dissolved in 60 ml of a 1 to 5 water-acetone mixture and the solution stirred under nitrogen as 1.0 g p-toluenesulfonic acid monohydrate is added and the solution is stirred at room temperature for about one hour and evaporated to dryness. The residue is treated with 25 ml water and 50 ml diethylether and the phases separated. The water phase is washed with an additional 25 ml diethylether and the organic phases combined. Concentration in diethylether and hexane yields a yellow oily residue product having the desired structure as confirmed by proton NMR analysis as follows:

| δ(ppm) | #H | Splitting Pattern |
|--------|----|--------------------|
| 9.42   | 1  | singlet            |
| 27.0   | 5  | multiplet          |
| 4.73   | 2  | doublet of quartets |
| 2.22   | 3  | singlet            |
| 1.72   | 3  | doublet of triplets |

EXAMPLE 8

(E)-4(3-Hydroxyphenoxy)-2-methyl-2-buten-1-al

A solution of 10.32 g resorcinol monoacetate in 40 ml sieve dried dimethyl formamide is stirred at ambient temperature under nitrogen as 18.7 g of solid potassium carbonate is added. After 5 minutes, a solution of 16.08 g (E)-4-bromo-1,1-diethoxy-2-methyl-2-butene in 40 ml sieve dried dimethyl formamide is added in dropwise fashion over a 30 minute period. During this addition, the solution becomes dark brown. After the addition is completed, the reaction mixture is stirred for 2½ hours at room temperature and is then poured into 700 ml 10% potassium carbonate at 0° C. The mixture is extracted with two 200 ml portions of diethylether and the extracts are combined and washed with four 200 ml portions of distilled water. Anhydrous magnesium sulfate and activated charcoal are added to the solution and it is allowed to stand for 30 minutes and is then filtered. The golden filtrate is evaporated to dryness to yield 11.36 g of dark yellow brown oil which is (E)-4(3-acetoxyphenoxy)-1,1-diethoxy-2-methyl-2-butene which is dissolved in 150 ml methanol and stirred under nitrogen as 50 ml 5% aqueous sodium hydroxide solution is added and stirred for about two hours. The reaction mixture is placed in a rotary evaporator and the methanol removed. The remaining mixture is diluted to 200 ml and extracted with 200 ml diethylether. The ether solution is evaporated to dryness. The solution is dried over magnesium sulfate and treated with activated charcoal and filtered to yield a bright yellow solution. The solution is evaporated and yields 3.41 g of yellow oily residue which is taken up in 30 ml of a 1:5 water-acetone mixture and stirred under nitrogen as 0.5 g p-tolunesulfonic acid monohydrate is added. After about 30 minutes, the solution is evaporated to dryness and 25 ml water and 25 ml ethyl acetate are added and the residue separated. The ethyl acetate phase is dried over magnesium sulfate, treated with activated charcoal and filtered and the filtrate evaporated to dryness to yield 2.5 g yellow, oily solid residue. The residue is extracted in 50 ml diethylether and the diethylether solution concentrated to yield a yellow solid which is purified by recrystallization from a methanol-water mixture to yield about 1.0 g light yellow solid product, m.p. 136°-38° C. Elemental Analysis. Calculated: C,68.74; H,6.29. Found: C,68.75; H,6.36.

EXAMPLE 9

Methyl (E)-4(3-hydroxyphenoxy)-2-methyl-2-buten-1-oate

A mixture of 1.00 g of (E)-4(3-hydroxyphenoxy)-2-methyl-2-buten-1-al, 7.31 g active manganese dioxide, 1.26 g sodium cyanide and 0.4 g glacial acetic acid in 40 ml methanol is stirred at room temperature for about 16 hours, filtered and the filtrate evaporated to dryness using an aspirator and a concentrated aqueous sodium hydroxide trap. During the volume reduction, the filtrate is stirred in a water bath at about 35° C. The red oil residue is treated with 50 ml diethylether and 50 ml distilled water and the mixture stirred vigorously for about one hour. The phases are separated and the water layer is washed with 50 ml diethylether. The organic layers are combined and washed with two 150 ml portions of distilled water. The ether layer is dried over anhydrous magnesium sulfate, treated with activated charcoal and filtered. The filtrate is evaporated to dryness to yield 0.68 g light yellow oil which crystallizes on standing which is taken up in 40 ml diethylether and heated under a stream of nitrogen as 15 ml hexanes is slowly added. When the volume reaches 25 ml, it is treated with activated charcoal and filtered. The filtrate is reduced in volume to 200 ml, allowed to cool to room temperature and is placed in a freezer. Bright yellow solid forms and is collected by nitrogen pressure filtration and is dried under a stream of nitrogen yielding 0.27 g product, m.p. 79°-81° C. Elemental Analysis. Calculated: C,64.85; H,6.35. Found: C,64.74; H,6.37.

EXAMPLE 10

(E)-4(1-Naphthyloxy)-2-methyl-2-buten-1-al

A mixture of 11.5 g (E)-4-(bromo-1,1-diethoxy)-2-methyl-2-butene, 13.8 g potassium carbonate and 7.20 g 1-naphthol in 50 ml sieve dried dimethyl formamide is stirred at room temperature under nitrogen for about 64 hours. The reaction mixture is poured into 300 ml distilled water and the mixture stirred for about 30 minutes before being extracted with two 200 ml portions of diethylether. The ether extracts are combined and washed with 200 ml of a 10% aqueous potassium carbonate solution and with 200 ml distilled water and is then treated with magnesium sulfate and activated carbon. Filtration yields a deep red solution which is evaporated to dryness to yield 12.05 g red oil. The oil is dissolved in 60 ml of a 1:5 water-acetone mixture and the solution is stirred at room temperature under nitrogen as 1.5 g p-toluenesulfonic acid monohydrate is added. After about one hour, the acetone is removed on the rotary evaporator and the red oily mixture is treated with 50 ml diethylether and distilled water and the phases separated. The water phase is washed with an additional 50 ml diethylether and the organic phases combined, treated with magnesium sulfate and activated carbon and filtered. The filtrate is evaporated to dryness and yields a red brown oil which gradually solidifies and is dissolved in 80 ml diethylether and the solution is reduced in volume to 40 ml by heating under a stream of nitrogen. Then 10 ml hexanes is added and the solution allowed to cool to room temperature before being placed in a freezer. A yellow solid precipitates and is collected by nitrogen pressure filtration and dried under a stream of nitrogen to yield 2.09 g solid product, m.p. 81.5°–82.5° C. Elemental Analysis. Calculated: C,79.62; H,6.24. Found: C,79.32; H,6.27.

PREPARATION A

(E)-4-Bromo-1,1-diethoxy-2-methyl-2-butene

To 200 ml of a 1:1 ethyl acetate-chloroform mixture is added 10.1 ml isoprene epoxide, 48.0 g copper (II) bromide and 7.5 g lithium carbonate and the mixture heated at reflux for about 35 minutes using a water bath does not exceed 85° C. The solution is then cooled to 5° C. in an ice bath and 100 ml distilled water is added. Stirring is continued for about 30 minutes and the mixture is then filtered to remove the precipitated copper (I) bromide. The filtrate is separated into an aqueous and an organic phase and the aqueous phase is washed with 150 ml hexanes. The hexane wash is combined with the organic phase. The solution is filtered and the light yellow solution is washed with three 150 ml portions water. The light yellow solution is then treated with anhydrous magnesium sulfate and filtered and the filtrate evaporated to dryness to yield a pale yellow oil which is (E)-4-bromo-2-methyl-2-buten-1-al. The product is stirred at room temperature under nitrogen as 17.0 ml of triethylorthoformate and 3.0 ml absolute ethanol are added. After about 42 hours, the ethanol and excess triethylorthoformate are removed using a water bath at 30° C. and a vacuum of 1.0 mm mercury over about a one hour period. About 16.08 g of a light oily residue is obtained which is confirmed to be (E)-4-bromo-1,1-diethoxy-2-methyl-2-butene by proton NMR analysis.

The compounds of this invention have plant growth regulating activities. The plant growth regulating effects are manifested as for example a stunting or dwarfing effect on the vegetative growth of plants. Such stunting or dwarfing may be useful, for example, in peanuts, cereals and soya bean where reduction in stem growth may reduce the risk of lodging and may also permit increased amounts of fertilizer to be applied. The stunting of woody species is useful in controlling the growth of undergrowth under power lines and the like. Compounds which induce stunting or dwarfing may also be useful in modifying the stem growth of sugar cane thereby increasing the concentration of sugar in the cane at harvest; in sugar cone, the flowering and ripening may be controllable by applying the compounds. Stunting of peanuts can assist in harvesting. Growth retardation of grasses can help maintenance of grass swards. The compounds may stunt grasses without significant phytotoxic effects and without deleteriously affecting the appearance, particularly the color, of the grass. This makes such compounds attractive for use on ornamental lawns and on grass verges. They may also have an effect on flower head emergence in for example grasses. The compounds may also stunt weed species present in the grasses; examples of such weed species are sedges such as Cyperus spp. and dicotyledonous weeds, for example, daisy, plantain, knotweed, speedwell, thistle, docks and ragwort. The growth of non-crop vegetation, for example, weeds or cover vegetation, may be retarded thus assisting in the maintenance of plantation and field crops. In fruit orchards, particularly orchards subject to soil erosion, the presence of grass cover is important. However, excessive grass growth requires substantial maintenance. The compounds of the invention could be useful in this situation as they could restrict growth without killing the plants which would lead to soil erosion. At the same time, the degree of competition for nutrients and water by the grass would be reduced and this could result in an increased yield of fruit. In some cases, one grass species may be stunted more than another grass species; this selectivity could be useful for example for improving the quality of a sward by preferential suppression of the growth of undesirable species.

The dwarfing may also be useful in miniaturizing ornamental, household, garden and nursery plants, for example, poinsettias, chrysanthemums, carnations, tulips and daffodils.

As indicated above, the compounds may also be used to stunt woody species. This property may be used to control hedgerows or to shape fruit trees, for example, apples.

The plant growth regulating effect may, as implied above, manifest itself in an increase in crop yield.

In the potato, vine control in the field and inhibition of sprouting in the store may be possible.

Other plant growth regulating effects caused by the compounds may include alteration of leaf angle and promotion of tillering in plants. The former effect may be useful for example in altering the leaf orientation of, for example, potato crops thereby letting more light into the crops and inducing an increase in photosynthesis and tuber weight. By increasing tillering in mono- and dicotyledonous crops, for example, rice, corn and soybeans, the number of flowering shoots per unit area may be increased thereby increasing the overall grain of such crops. In grass swards an increase in tillering could lead to a denser sward which may result in increased resilience in wear.

The treatment of plants with the compounds may lead to the leaves developing a darker green color and delay senescence in crops thereby leading to improved pod fill in soybean for example.

The compounds may inhibit, or at least delay, the flowering of sugar beet and thereby may increase sugar yield. They may also reduce the size of sugar beet without reducing significantly the sugar yield thereby enabling an increase in planting density to be made. Similarly, in other root crops, such as, for example, turnip, swede, mangold, parsnip, beetroot, yam and cassava, it may be possible to increase the planting density.

The compounds could be useful in restricting the vegetative growth of cotton thereby leading to an increase in cotton yield.

The compounds may be useful in rendering plants resistant to stress since the compounds may delay the emergence of plants grown from seed, shorten stem height and delay flowering. These properties could be useful in preventing frost damage in countries where there is significant snow cover in the winter since then the treated plants would remain below the snow cover during the cold weather. Further the compounds may provide drought or cold resistance in certain plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.05 to 20, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds may be used as such plant growth regulating purposes but are more conveniently formulated into compositions for such usage. The invention thus provides also a plant growth regulating composition comprising a compound of Formula 1 or 2 or a phytopharmaceutically acceptable salt thereof as hereinbefore defined, and an inert carrier or diluent.

It also provides a method of regulating the growth of a plant which method comprises applying to the plant, to seed of the plant or to the locus of the plant or seed a plant growth regulating compound as hereinbefore defined.

The plant growth regulating compounds of this invention can be applied in a number of ways, for example they can be formulated for unformulated, directly to the foliage of a plant, or they can be applied also to bushes and trees, to seeds or to other media in which plants, bushes or trees are growing or are to be planted, or they can be sprayed on, dusted on or applied as a cream or paste formulation, or they can be applied as a vapor. Application can be to any part of the plant, bush or tree, for example to the foliage, stems, branches or roots, or to soil surrounding the roots, for systemic activity, or to the seed before it is planted.

The term "plant" as used herein includes seedlings, bushes and trees.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, keiselguhr, dolomite, calcium carbonate, talc, powdered magnesia, Fuller's earth, gypsum Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent, for example, a mineral oil, for assisting the adhesion of the composition to the seed. Alternatively the active ingredient can be formulated for seed dressing purposes using an organic solvent, for example N-methylpyrrolidone or dimethylformamide.

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient in an organic solvent optionally containing wetting, dispersing or emulsifying agents and then adding the mixture to water which may also contain wetting, dispersing or emulsifying agents. As example of suitable organic solvents there may be mentioned, for example, ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers such as 2-ethoxyethanol and 2-butoxyethanol.

The compositions to be used as sprays may also be in the form of aerosols wherein the formulation is held in a container under pressure in the presence of a propellant, such as, for example, fluorotrichloromethane or dichlorodifluoromethane.

The plant growth regulating compounds can be mixed in the dry state with a pyrotechnic mixture to form a composition suitable for generating in enclosed spaces a smoke containing the compounds. Alternatively, the compounds may be used in a micro-encapsulated form.

By including suitable additives, for example additives for improving the distribution, adhesive power and resistance to rain on treated surfaces, the different compositions can be better adapted for various utilities.

The plant growth regulating compounds can also be used as mixtures with fertilizers. Compositions comprising only granules of fertilizer incorporating, for example coated with, the plant growth regulating compound, are preferred. Such granules suitably contain up to 25% by weight of the compound. The invention therefore also provides a fertilizer composition comprising the plant growth regulation compound of Formula 1.

The compositions may also be in the form of liquid preparations for use as dips or sprays which are generally aqueous dispersions or emulsions containing the active ingredient in the presence of one or more surfactants, for example, wetting agents, dispersing agents, emulsifying agents or suspending agents. These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulfuric acid, for example sodium lauryl sulfate, and salts of sulfonated aromatic compounds, for example sodium dodecylbenzenesulfonate, sodium, calcium or ammonium lignosulfonate, butylnaphthalene sulfonate, and a mixture of sodium diisopropyl- and triisopropyl-naphthalene sulfonates.

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the acid partial esters with ethylene oxide, and the lecithins. Suitable suspending agents are hydrophilic colloids, for example polyvinylpyrrolidone and sodium carboxymethylcellulose, and the vegetable gums, for example gum acacia and gum tragacanth.

The compositions for use as aqueous dispersions or emulsions are generally supplied in the form of a concentrate containing a high proportion of the active ingredient. The concentrates are then diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25-60%, by weight of the active ingredient. These concentrates suitably contain organic acids, for example, alkaryl or aryl sulfonic acids such as xylenesulfonic acid or dodecylbenzenesulfonic acid, since the presence of such acids can increase the solubility of the active ingredient in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention can comprise also other compounds having biological activity, for example, compounds having similar or complementary plant growth regulating activity or compounds having herbicidal or insecticidal or fungicidal activity.

The fungicidal compound can be for example one which is capable of combatting ear diseases of cereals such as wheat, seed and soil borne diseases and downy and powdery mildews on grapes and powdery mildew and scab on apple and the like. Examples of the other fungicidal compounds are imazalil, benomyl, carbendazim (BCM), thiophanate-methyl, captafol, captan, sulphur, dithiocarbamates, carbathiins, copper oxychloride, triforine, dodemorph, tridemorph, dithianon, pyrazophos, binapacryl, quinomethionate, panoctine, furalaxyl, aluminum tris(ethyl phosphonate), DPX3217, ethirimol, dimethirimol, bupirimate, chlorothalonil, Chevron RE 20615, vinclozolin, procymidone, iprodione and metaxanine.

The other plant growth regulating compound can be one which controls weeds or seedhead formation, improves the level or longevity of the plant growth regulating activity of the compounds of this invention, selectively controls the growth of the less desirable plants such as grasses or causes the plant growth regulating compound of Formula 1 to act faster or slower as a plant growth regulating agent. Some of these other agents will be herbicides. Examples of suitable agents are the gibberellins such as $GA_3$, $GA_4$, or $GA_7$, the auxins such as indoleacetic acid, indolebutyric acid, naphthoxyacetic acid or naphthylacetic acid, phenoxyacetic acids such as 2,4-D or MCPA, substituted benzoic acids such as TIBA and morphactins such as chlorfluorecol, and the cytokinins such as kinetin, and benzyladenine, and the cytokinin-like compounds, diphenylurea, and benzimidazole. Also included would be maleic hydrazide, glyphosate, glyphosine, long chain fatty alcohols and acids, dikegulac, substituted quaternary ammonium and phosphonium compounds such as CCC or Phosfon-D, carbetamide, asulam, abscissic acid, isopyrimol, and hydroxybenzonitriles such as bromoxynil.

Utilizing the compounds of this invention as the active ingredients in plant growth regulating compositions, said compounds were found to possess plant growth regulating activity when tested in accordance with the following test procedures.

TEST A—Soybean Cotyledon Callus Growth Bioassay

Cytokinin type activity is illustrated by a soybean cotyledon callus bioassay test comprising the following procedure. Growth medium employed in this test is obtained in the following manner. One liter of growth medium is prepared by adding 10 ml of each of the sixteen following stock solutions to a two liter flask containing 250 ml of water:

| Stock Solution No. | Description |
| --- | --- |
| 1 | 30 grams $KH_2PO_4$ in 500 ml water |
| 2 | 100 grams $KNO_3$ in 500 ml water |
| 3 | 100 grams $NH_4NO_3$ in 500 ml water |
| 4 | 50 grams $Ca(NO_3)_2 \cdot 4H_2O$ in 500 ml water |
| 5 | 7.15 grams $MgSO_4 \cdot 7H_2O$ in 500 ml water |
| 6 | 6.5 grams KCl in 500 ml water |
| 7 | 1.4 grams $MnSO_4 \cdot 4H_2O$ in 500 ml water |
| 8 | Dissolve 1340 mg EDTA $Na_2 \cdot 2H_2O$ in 500 ml water and heat; while still hot add 990 mg $Fe_2SO_4 \cdot 7H_2O$ and stir into solution |
| 9 | 380 mg $ZnSO_4$ $7H_2O$ in 500 ml water |
| 10 | 160 mg $H_3BO_3$ in 500 ml water |
| 11 | 75 mg KI in 500 ml water |
| 12 | 35 mg $Cu(NO_3)_2 \cdot 3H_2O$ in 500 ml water |
| 13 | 10 mg $(NH_4)_6Mo_7O_{24} \cdot 4H_2O$ in 500 ml water |
| 14 | 10 grams i-inositol in 50 mg water |
| 15 | 50 mg nicotinic acid, 20 mg pyridoxine . HCl and 20 mg thiamin . HCl in 500 ml water |
| 16 | 40 mg α-naphthaleneacetic acid in 100 ml water. |

To said two liter flask is added 30 grams sucrose and the volume is adjusted to 450 ml and to pH 5.8 and thereafter the volume is adjusted to 500 ml with deionized water.

Into each of seven 500 ml flasks (numbered 1 through 7) there is placed 125 ml of growth medium. Flask number 1 is adjusted to 250 ml volume by the addition of deionized water and serves as the growth medium control. Into each of flasks number 2 and 3 there is added 6.5 ml of 22 mg/l kinetin stock solution and each of the flasks volume is adjusted to 250 ml by the addition of deionized water. Flask 2 serves as the kinetin reference standard. Deionized water is added to each of flasks 4 through 7 to adjust the volume of each to 250 ml. This is followed by the addition and solubilization of 2.5 g Difco Bacto-Agar in each of the seven flasks. All seven flasks and their contents are then sterilized in an autoclave at 121° C. and 15 psi for 15 minutes. Filtered (Millipore) and sterilized solutions of test compound are added to flasks 3 through 7 in amounts to result in a final concentration of test compound in the flasks in the following amounts:

Flask 3—50 mg/l test compound (plus kinetin)
Flask 4—0.05 mg/l test compound
Flask 5—0.5 mg/l test compound
Flask 6—5 mg/l test compound
Flask 7—50 mg/l test compound, From each of the seven 500 ml flasks 50 ml of solution is withdrawn and deposited asceptically into seven respectively numbered sterile 125 ml flasks and plugged with cotton. To each 125 ml flask is added three small, approximately 5 mg fresh weight, soybean cotyledon callus pieces. The flasks are placed in a growth chamber at 27°-30° C. for twenty seven days after which the callus is removed and observed for size and weight.

TEST B—Chlorophyll Retention Test

Six petri dishes are prepared by placing the following solutions into the respective dishes.

| Petri Dish No. | Solution |
| --- | --- |
| 1 | 25 ml distilled water |

-continued

| Petri Dish No. | Solution |
|---|---|
| 2 | 25 ml aqueous solution of 5 mg/l kinetin |
| 3 | 25 ml aqueous solution of 5 mg/l kinetin and 50 mg/l test compound |
| 4 | 25 ml aqueous solution of 0.5 mg/l test compound |
| 5 | 25 ml aqueous solution of 5 mg/l test compound |
| 6 | 25 ml aqueous solution of 50 mg/l test compound |

Approximately 1 g of previously cut leaves (for example, 7 to 9 day old wheat, oat or barley, but preferably oat) is floated on the solution in each petri dish. The petri dishes are stored under light of about 25 ft-candles at 27°–30° C. for approximately seven days. The leaves from each petri dish are then analyzed for the amount of chlorophyll retained in the leaves according to the following procedure. The chlorophyll is extracted from the leaves with several washes of 80% acetone at a total volume equivalent to 1 ml acetone for every 10 mg fresh weight of plant leaves after the last extraction. When the leaves appear to be free of green pigment, the total volume is adjusted with 100% acetone to accomodate for evaporative loss during extraction. Optical density readings on a spectrophotometer are taken of the extract against a solvent blank (80% acetone) at wavelengths of 645 and 663 nm. The amount of chlorophyll is calculated with the following equation:

$$\text{Mg total chlorophyll/g tissue} = [20.2(D_{645}) + 8.02(D_{663})] \frac{V}{1000 \times W}$$

wherein
D = optical density or absorbance
V = final volume of 80% acetone/chlorophyll extract
W = fresh weight in grams of the tissue extracted.

The following table summarizes the results and observations made in accordance with the hereinbefore set forth Tests A and B.

TABLE

| Compound of Example No. | Test | Concentration of Test Compound | Observation |
|---|---|---|---|
| 1 | A | 50 mg/l | inhibits action of kinetin in inducing callus growth |
| 2 | B | 50 mg/l | decreases chlorophyll retention activity of kinetin |
|   | B | 50 mg/l | reduces chlorophyll retention |
| 3 | A | 50 mg/l | inhibits action of kinetin in inducing callus growth |
| 4 | A | 50 mg/l | inhibits action of kinetin in inducing callus growth |
|   | B | 50 mg/l | decreases chlorophyll retention activity of kinetin |
|   | B | .5 mg/l | increases chlorophyll retention |
| 5 | B | 5 mg/l | decreases chlorophyll retention activity of kinetin |
|   | B | 5 mg/l | reduces chlorophyll retention |
| 6 | B | 50 mg/l | decreases chlorophyll retention |
| 7 | A | 50 mg/l | inhibits action of kinetin in inducing callus growth |
| 8 | A | 50 mg/l | inhibits action of kinetin in inducing callus growth |
|   | B | 50 mg/l | decreases chlorophyll retention activity of kinetin |
| 9 | A | 50 mg/l | inhibits action of kinetin in inducing callus growth |
|   | B | 50 mg/l | decreases chlorophyll retention activity of kinetin |
| 10 | B | 50 mg/l | decreases chlorophyll retention activity of kinetin |

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

We claim:

1. A 4-phenoxy-2-butene compound of the formula

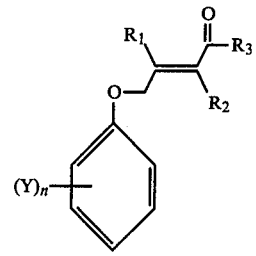

and phytopharmaceutically acceptable salts thereof, wherein $R_1$ and $R_2$ are selected from hydrogen and —$CH_3$ with the proviso that one of $R_1$ and $R_2$ is —$CH_3$ and the other is hydrogen; $R_3$ is hydrogen Y is selected from the group consisting of (lower)alkyl, halo, nitro, —$CF_3$, —S—(lower)alkyl, —O—(lower)alkyl, —O—acetyl, hydroxy, —NH—acetyl, amino, —NH(lower)alkyl, —N—di(lower)alkyl, and a fused benzene ring; and n is equal to 0, 1 or 2, wherein the term (lower)alkyl as used in the foregoing definitions includes straight or branched chain alkyl radicals containing from 1 to 6 carbon atoms.

2. A compound of the formula of claim 1 wherein $R_1$ is hydrogen and $R_2$ is —$CH_3$; Y is selected from the group consisting of halo, —O—(lower)alkyl, —O—acetyl, hydroxy, —NH—acetyl and a fused benzene ring; and n is equal to 1 or 2.

3. A compound of claim 2 wherein Y is halo selected from chlorine or bromine.

4. A compound of claim 3 wherein Y is chlorine and n is equal to 2 and the Y's are in the 2- and 4-positions on the phenyl ring.

5. A compound of claim 2 which is (E)-4(3-acetamidophenoxy)-2-methyl-2-buten-1-al.

6. A compound of claim 2 which is (E)-4(4-acetamidophenoxy)-2-methyl-2-buten-1-al.

7. A compound of claim 2 which is (E)-4(3-methoxyphenoxy)-2-methyl-2-buten-1-al.

8. A compound of claim 4 which is (E)-4(2,4-dichlorophenoxy)-2-methyl-2-buten-1-al.

9. A compound of claim 2 which is (E)-4(3-hydroxyphenoxy)-2-methyl-2-buten-1-al.

10. A compound of claim 2 which is (E)-4(3-acetoxyphenoxy)-2-methyl-2-buten-1-al.

11. A compound of claim 2 which is (E)-4(1-naphthyloxy)-2-methyl-2-buten-1-al.

12. A method of regulating the growth of leguminous plants which comprises applying to the plant locus a plant growth regulating effective amount of a 4-phenoxy-2-butene compound of the formula

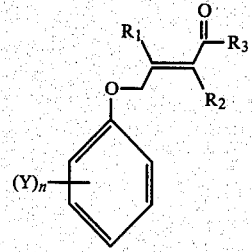

and phytopharmaceutically acceptable salts thereof, wherein $R_1$ and $R_2$ are selected from hydrogen and —$CH_3$ with the proviso that one of $R_1$ and $R_2$ is —$CH_3$ and the other is hydrogen; $R_3$ is hydrogen; Y is selected from the group consisting of (lower)alkyl, halo, nitro, —$CF_3$, —S—(lower)alkyl, —O—(lower)alkyl, —O—acetyl, hydroxy, —NH—acetyl, amino, —NH(lower)alkyl, —N—di(lower)alkyl, and a fused benzene ring; and n is equal to 0, 1 or 2, wherein the term (lower)alkyl is used in the foregoing definitions includes straight or branched chain alkyl radicals containing from 1 to 6 carbon atoms.

13. The method of claim 12 wherein $R_1$ is hydrogen and $R_2$ is —$CH_3$; Y is selected from the group consisting of halo, —O—(lower)alkyl, —O—acetyl, hydroxy, —NH—acetyl and a fused benzene ring; and n is equal to 1 or 2.

14. The method of claim 13 wherein Y is halo selected from chlorine and bromine.

15. The method of claim 14 wherein Y is chlorine and n is equal to 2 and the Y's are in the 2- and 4-positions on the phenyl ring.

16. The method of claim 15 wherein the 4-phenoxy-2-buten-1-al compound is (E)-4(2,4-dichlorophenoxy)-2-methyl-2-buten-1-al.

17. The method of claim 12 wherein the compound is applied to the plant locus in an amount of from about 0.05 to about 20 kg/hectare.

18. The method of claim 13 wherein the compound is applied to the plant locus in an amount of from about 0.05 to about 20 kg/hectare.

19. The method of claim 14 wherein the compound is applied to the plant locus in an amount of from about 0.05 to about 20 kg/hectare.

20. The method of claim 15 wherein the compound is applied to the plant locus in an amount of from about 0.05 to about 20 kg/hectare.

21. The method of claim 16 wherein the compound is applied to the plant locus in an amount of from about 0.05 to about 20 kg/hectare.

22. A plant growth regulating composition comprising an inert carrier material and from about 5 to about 95 parts by weight of a plant growth regulating compound selected from a 4-phenoxy-2-butene compound of the formula

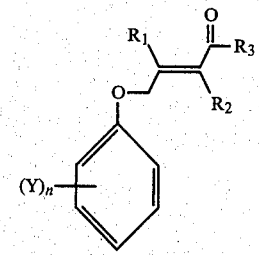

and phytopharmaceutically acceptable salts thereof, wherein $R_1$ and $R_2$ are selected from hydrogen and —$CH_3$ with the proviso that one of $R_1$ and $R_2$ is —$CH_3$ and the other is hydrogen; $R_3$ is hydrogen; Y is selected from the group consisting of (lower)alkyl, halo, nitro, —$CF_3$, —S—(lower)alkyl, —O—(lower)alkyl, —O—acetyl, hydroxy, —NH—acetyl, amino, —NH(lower)alkyl, —N—di(lower)alkyl, and a fused benzene ring; and n is equal to 0, 1 or 2, wherein the term (lower)alkyl as used in the foregoing definitions includes straight or branched chain alkyl radicals containing from 1 to 6 carbon atoms.

23. The plant growth regulating composition of claim 22 wherein $R_1$ is hydrogen and $R_2$ is —$CH_3$; Y is selected from the group consisting of halo, —O—(lower)alkyl, —O—acetyl, hydroxy, —NH—acetyl and a fused benzene ring; n is equal to 1 or 2.

24. The plant growth regulating composition of claim 23 wherein Y is halo selected from chlorine and bromine.

25. The plant growth regulating composition of claim 24 wherein Y is chlorine and n is equal to 2 and the Y's are in the 2- and 4-positions on the phenyl ring.

26. The plant growth regulating composition of claim 25 wherein the 4-phenoxy-2-buten-1-al compound is (E)-4(2,4-dichlorophenoxy)-2-methyl-2-buten-1-al.

* * * * *